US009562237B2

(12) United States Patent
Yang

(10) Patent No.: US 9,562,237 B2
(45) Date of Patent: Feb. 7, 2017

(54) REDUCTION OF TGF BETA SIGNALING IN MYELOID CELLS IN THE TREATMENT OF CANCER

(71) Applicant: The United States of America, as represented by the Secretary, Department of Health and Human Services, Washington, DC (US)

(72) Inventor: Li Yang, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/820,697

(22) Filed: Aug. 7, 2015

(65) Prior Publication Data

US 2015/0344891 A1 Dec. 3, 2015

Related U.S. Application Data

(62) Division of application No. 13/589,769, filed on Aug. 20, 2012, now Pat. No. 9,115,371.

(60) Provisional application No. 61/525,025, filed on Aug. 18, 2011.

(51) Int. Cl.
| | | |
|---|---|---|
| A61K 48/00 | (2006.01) | |
| C12N 15/85 | (2006.01) | |
| C12Q 1/68 | (2006.01) | |
| G01N 33/50 | (2006.01) | |
| G01N 33/574 | (2006.01) | |
| A61K 31/5377 | (2006.01) | |
| A61K 31/7088 | (2006.01) | |
| C12N 15/113 | (2010.01) | |
| C07K 14/71 | (2006.01) | |
| A61K 35/15 | (2015.01) | |
| A61K 35/28 | (2015.01) | |
| A01K 67/027 | (2006.01) | |

(52) U.S. Cl.
CPC ........... *C12N 15/85* (2013.01); *A01K 67/0276* (2013.01); *A61K 31/5377* (2013.01); *A61K 31/7088* (2013.01); *A61K 35/15* (2013.01); *A61K 35/28* (2013.01); *C07K 14/71* (2013.01); *C12N 15/1138* (2013.01); *C12Q 1/6886* (2013.01); *G01N 33/5091* (2013.01); *G01N 33/57492* (2013.01); *A01K 2217/075* (2013.01); *A01K 2217/206* (2013.01); *A01K 2227/105* (2013.01); *A01K 2267/0331* (2013.01); *C12N 2310/14* (2013.01); *C12N 2320/30* (2013.01); *C12Q 2600/158* (2013.01); *G01N 2333/71* (2013.01)

(58) Field of Classification Search
CPC .................................................... A61K 48/00
See application file for complete search history.

(56) References Cited

PUBLICATIONS

U.S. Appl. No. 13/589,769, filed Aug. 20, 2012.
Achyut et al., "Stromal depletion of transforming growth factor receptor 2 promotes the development of forestomach squamous cell carcinoma," *AACR Presentation Abstract* 3969 (Apr. 2010).
Almand et al., "Increased Production of Immature Myeloid Cells in Cancer Patients: A Mechanism of Immunosuppression in Cancer," *J. Immunol.*, 166, 678-689 (2001).
Balkwill et al., "An inflammatory link," *Nature*, 431, 405-406 (2004).
Bhowmick et al., "TGF-β Signaling in Fibroblasts Modulates the Oncogenic Potential of Adjacent Epithelia," *Science*, 303 (5659), 848-851 (2004).
Biswas et al., "Transforming Growth Factor β Receptor Type II Inactivation Promotes the Establishment and Progression of Colon Cancer," *Cancer Res.*, 64: 4687-4692 (2004).
Chalmin et al., "Membrane-associated Hsp72 from tumor-derived exosomes mediates STAT3-dependent immunosuppressive function of mouse and human myeloid-derived suppressor cells," *J. Clin. Invest.*, 120 (2), 457-471 (2010).
Chytil et al., "Conditional Inactivation of the TGF—Type II Receptor Using Cre:Lox," *Genesis*, 32, 73-75 (2002).
Dumont et al., "Targeting the TGFβ signaling network in human neoplasia," *Cancer Cell*, 3, 531-536 (2003).
Flavell et al., "The polarization of immune cells in the tumour environment by TGFβ," *Nat. Rev. Immunol.*, 10, 554-567 (2010).
Forrester et al., "Effect of Conditional Knockout of the Type II TGF-β Receptor Gene in Mammary Epithelia on Mammary Gland Development and Polyomavirus Middle T Antigen Induced Tumor Formation and Metastasis," *Cancer Res.*, 65: 2296-2302 (2005).
Fridlender et al., "Polarization of Tumor-Associated Neutrophil Phenotype by TGF-b: "N1" versus "N2" TAN," *Cancer Cell*, 16, 183-194 (2009).
Gabrilovich et al., "Myeloid-derived suppressor cells as regulators of the immune system," *Nat. Rev. Immunol.*, 9 (3), 162-174 (2009).
Genbank Accession Nos. NM_001024847 (printed Aug. 11, 2012).

(Continued)

*Primary Examiner* — Kimberly Chong
(74) *Attorney, Agent, or Firm* — Leydig, Voit & Mayer, Ltd.

(57) ABSTRACT

Methods of inhibiting metastasis in cancer patients are provided, wherein the methods comprise reducing TGFβ signaling, for example, by reducing TGFβ receptor II expression in myeloid cells. Vectors comprising a TGFβ receptor II RNAi nucleic acid sequence operably linked to a myeloid specific promoter also are provided. A method of diagnosing cancer in an individual by determining TGFβ receptor II expression in myeloid cells in the individual is provided. Additionally, a method of modulating TGFβ activity in myeloid cells in a cancer patient comprising administering a regulator of at least one of the GSK3 and PI3K pathways to the patient is provided.

6 Claims, 23 Drawing Sheets

(56) References Cited

PUBLICATIONS

Genbank Accession Nos. NM_003242 (printed Aug. 11, 2012).
Gorelik et al., "Immune-mediated eradication of tumors through the blockade of transforming growth factor-β signaling in T cells," *Nat. Med.*, 7 (10), 1118-1122 (2001).
Hazenbos et al., "GPI-anchor deficiency in myeloid cells causes impaired Fc R effector functions," *Blood*, 104, 2825-2831 (2004).
Hoechst et al., "Myeloid Derived Suppressor Cells Inhibit Natural Killer Cells in Patients with Hepatocellular Carcinoma via the NKp30 Receptor," *Hepatology*, 50, 799-807 (2009).
Kaplan et al., "VEGFR1-positive haematopoietic bone marrow progenitors initiate the pre-metastatic niche," *Nature*, 438, 820-827 (2005).
Kim et al., "Smad4 signalling in T cells is required for suppression of gastrointestinal cancer," *Nature*, 441 (7096), 1015-1019 (2006).
Lu et al., "Loss of transforming growth factor-β type II receptor promotes metastatic head-and-neck squamous cell carcinoma," *Genes and Development*, 20: 1331-1342 (2006).
Mantovani, "Inflaming metastasis," *Nature*, 457 (7225), 36-37 (2009).
McCormick, "Cancer Gene Therapy: Fringe or Cutting Edge?," *Nat. Rev. Cancer*, 1, 130-141 (2001).
Muraoka et al., "Blockade of TGFβ inhibits mammary tumor cell viability, migration, and metastases," *Journal of Clinical Investigation*, 109 (12)1551-1559 (2002).
Pan et al., "CXCR3/CXCR3 Ligand Biological Axis Impairs RENCA Tumor Growth by a Mechanism of Immunoangiostasis," *J. Immunol.*, 176, 1456-1464 (2006).
Pang et al., "Deletion of TGFβ signaling in Gr-1+CD11b+ myeloid cells attenuates breast adenocarcinoma progression," AACR Presentation Abstract 5320 (Apr. 2010).
Pang et al., "TGFβ signaling in Gr-1+CD11b+ myeloid cells is required for breast adenocarcinoma progression," AACR Poster Abstract 5320 (Apr. 2010).
Pollard, "Trophic macrophages in development and disease," *Nat. Rev. Immunol.*, 9 (4), 259-270 (2009).
Scanlon, "Cancer Gene Therapy: Challenges and Opportunities," *Anticancer Res.*, 24, 501-504 (2004).
Shah et al., "Suppression of Tumor Metastasis by Blockade of Transforming Growth Factor β Signaling in Bone Marrow Cells through a Retroviral-mediated Gene Therapy in Mice," *Cancer Res.*, 62, 7135-7138 (2002).
Sinha et al., "Mouse Lysozyme-M Knockout Mice Reveal How the Self-Determinant Hierarchy Shapes the T Cell Repertoire against This Circulating Self Antigen in Wild-Type Mice," *J. Immunol.*, 173, 1763-1771 (2004).
Srivastava et al., "Lung cancer patients' CD4+ T cells are activated in vitro by MHC II cell-based vaccines despite the presence of myeloid-derived suppressor cells," *Cancer Immunol. Immunother.*, 57 (10), 1493-1504 (2008).
Sun et al., "Rac1 is the small GTPase responsible for regulating the neutrophil chemotaxis compass," *Blood*, 104, 3758-3765 (2004).
Wesolowska et al., "Microglia-derived TGFβ as an important regulator of glioblastoma invasion—an inhibition of TGFβ-dependent effects by shRNA against human TGFβ type II receptor," *Oncogene*, 27: 918-930 (2008).
Yan et al., "Gr-1+CD11b+ Myeloid Cells Tip the Balance of Immune Protection to Tumor Promotion in the Premetastatic Lung," *Cancer Res.*, 70, 6139-6149 (2010).
Yang et al, "TGF-β and immune cells: an important regulatory axis in the tumor microenvironment and progression," *Trends Immunol.*, 31 (6), 220-227 (2010).
Yang et al., "Abrogation of TGFb Sigaling in Mammary Carcinomas Recruits Gr-1+CD11b+ Myeloid Cells that Promote Metastasis," *Cancer Cell*, 13, 23-35 (2008).
Yang et al., "Expansion of myeloid immune suppressor Gr+CD11b+ cells in tumor-bearing host directly promotes tumor angiogenesis," *Cancer Cell*, 6, 409-421 (2004).
Yang et al., "Transforming Growth Factor B: Tumor Suppressor or Promoter? Are Host Immune Cells the Answer?," *Cancer Res.*, 68 (22), 9107-9111 (2008).
Yang et al., "TGFβ, an inflammation and immune suppressor in tumor microenvironment and progression," AACR poster (Apr. 2010).
Yang et al., "TGFβ, an inflammation and immune suppressor in tumor microenvironment and progression," AACR Presentation Abstract 1344 (Apr. 2010).
Zea et al., "Arginase-Producing Myeloid Suppressor Cells in Renal cell Carcinoma Patients: A Mechanism of Tumor Evasion," *Cancer Res.*, 65, 3044-3048 (2005).

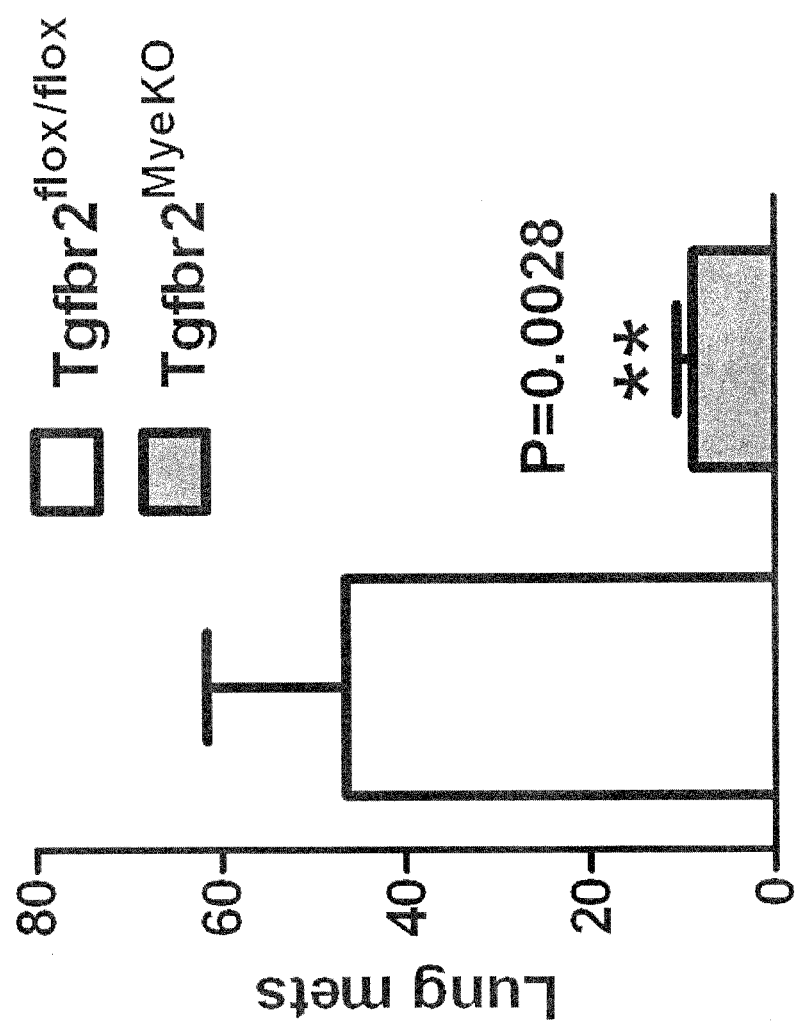

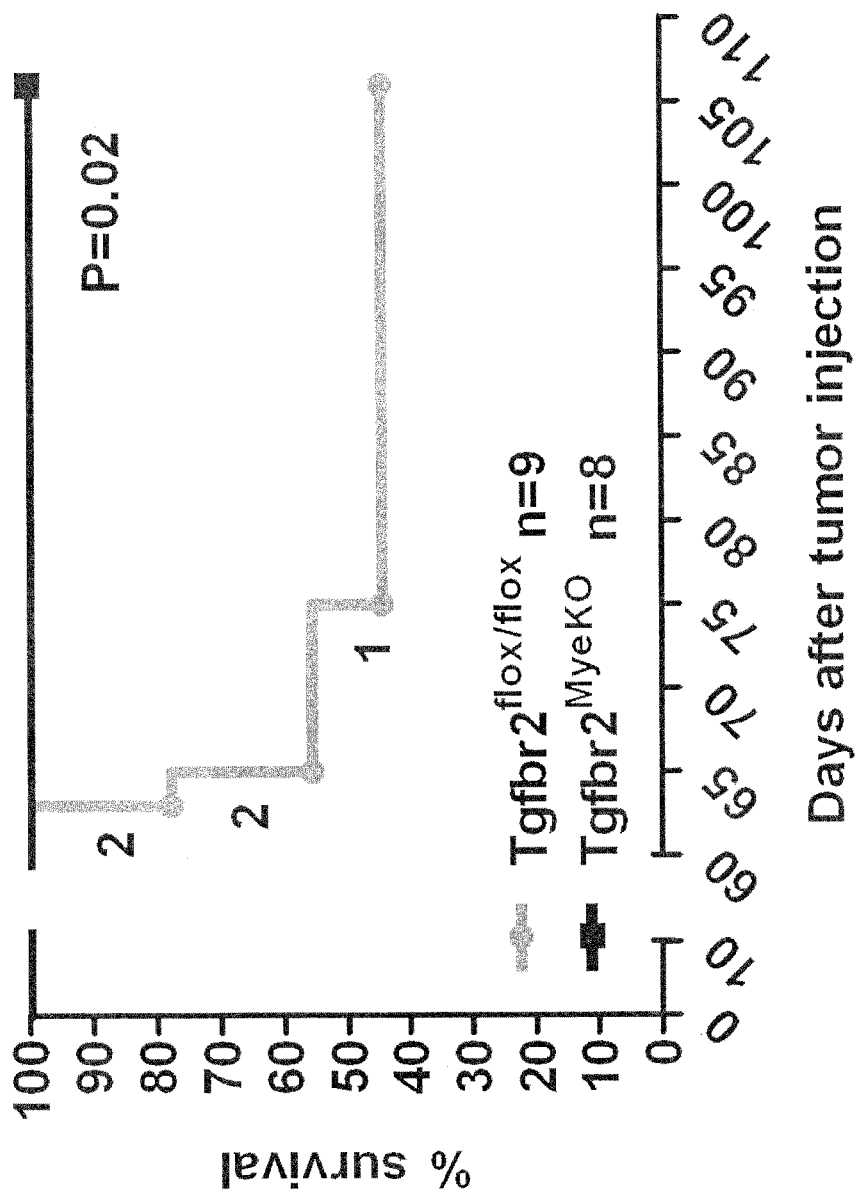

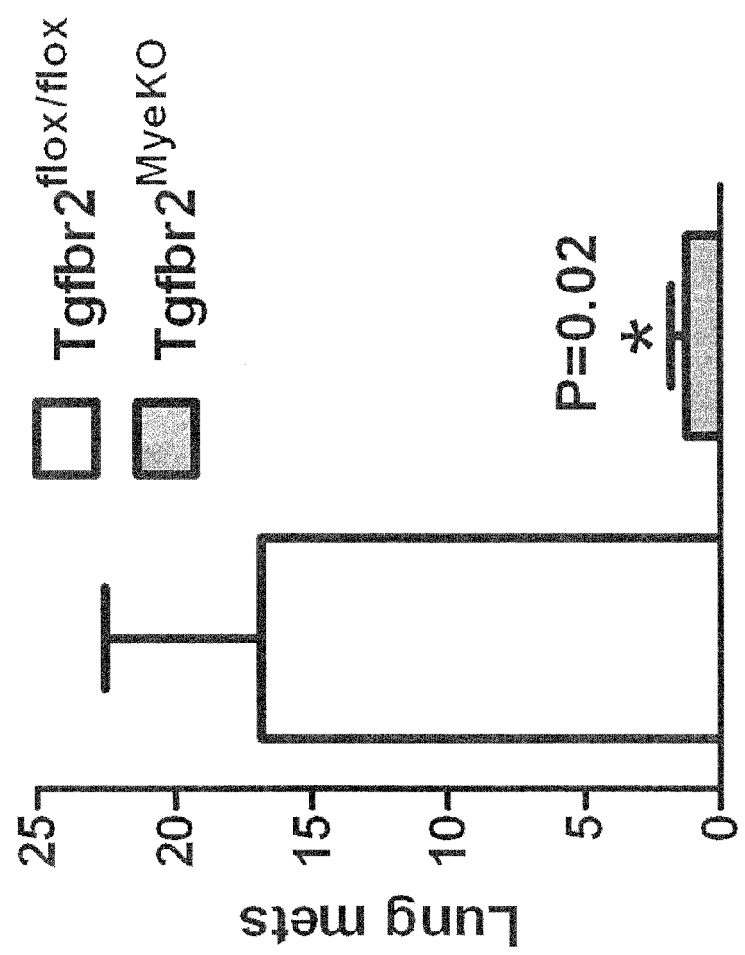

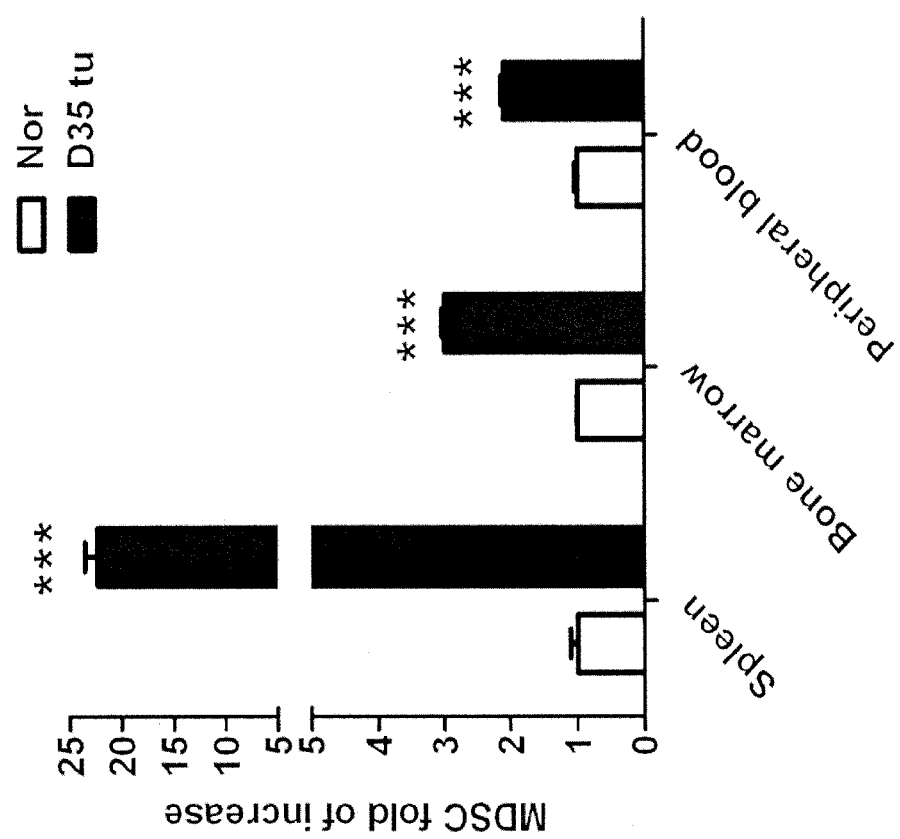

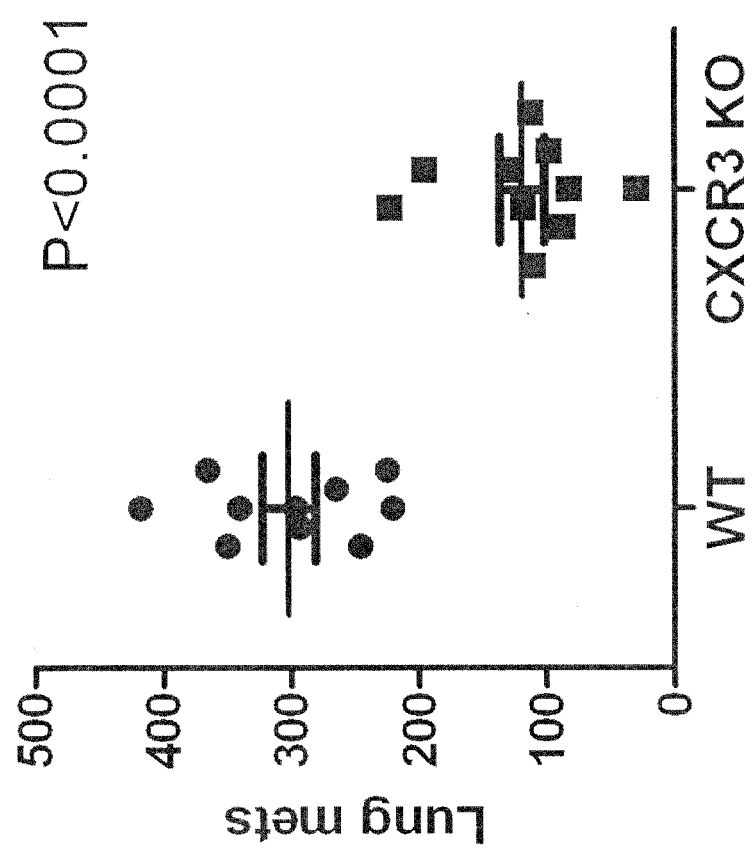

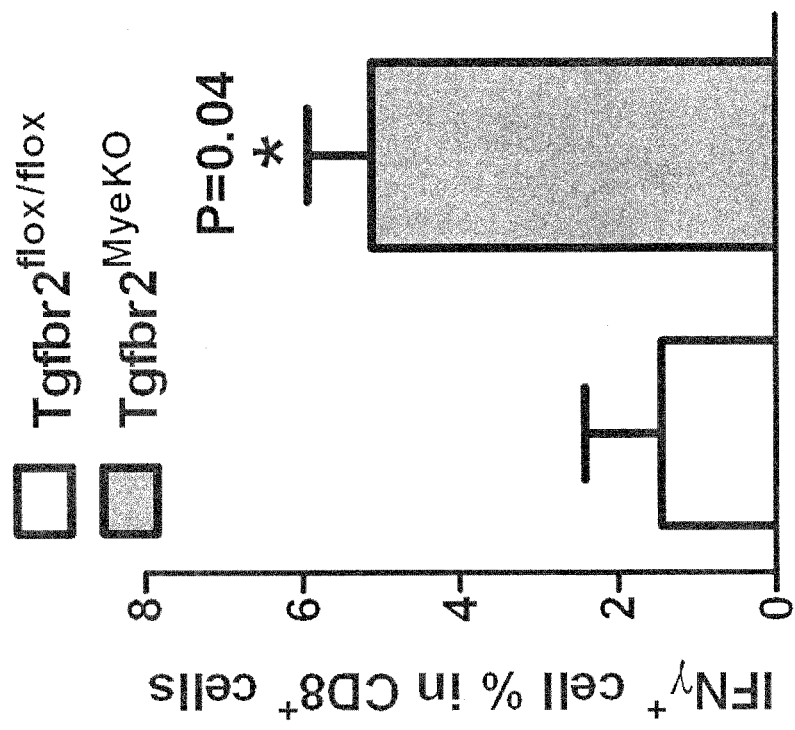

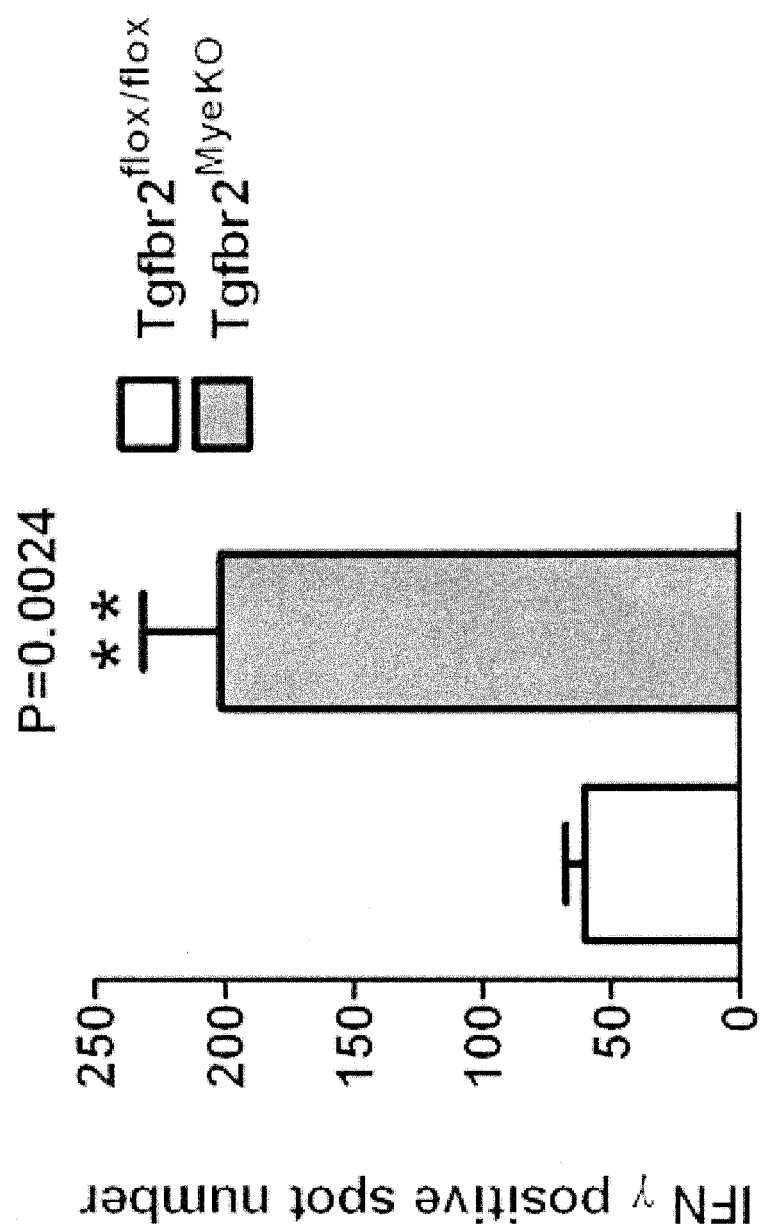

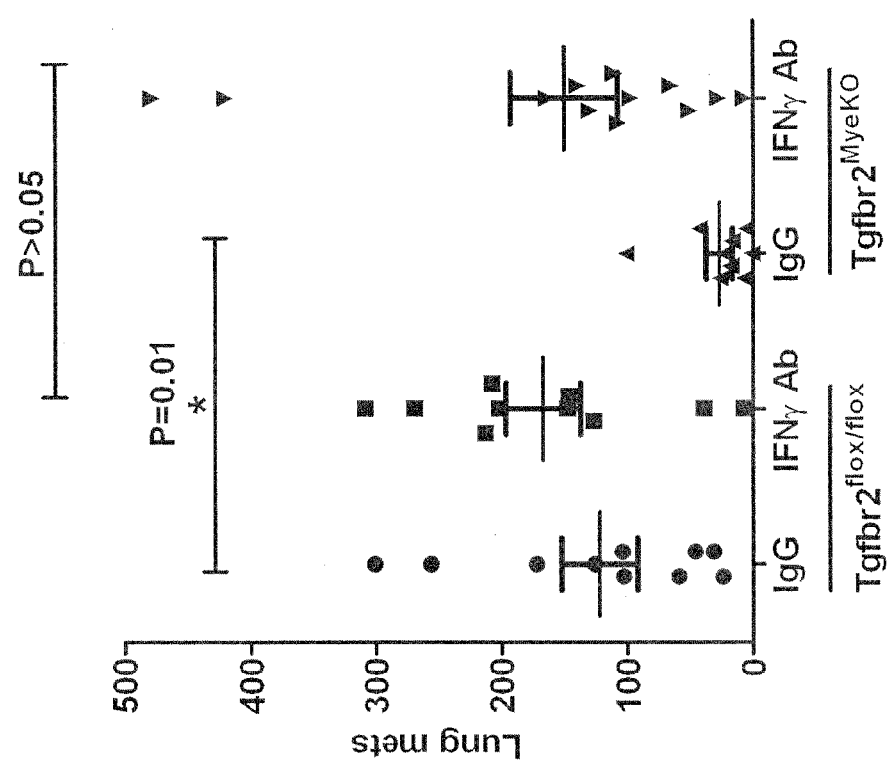

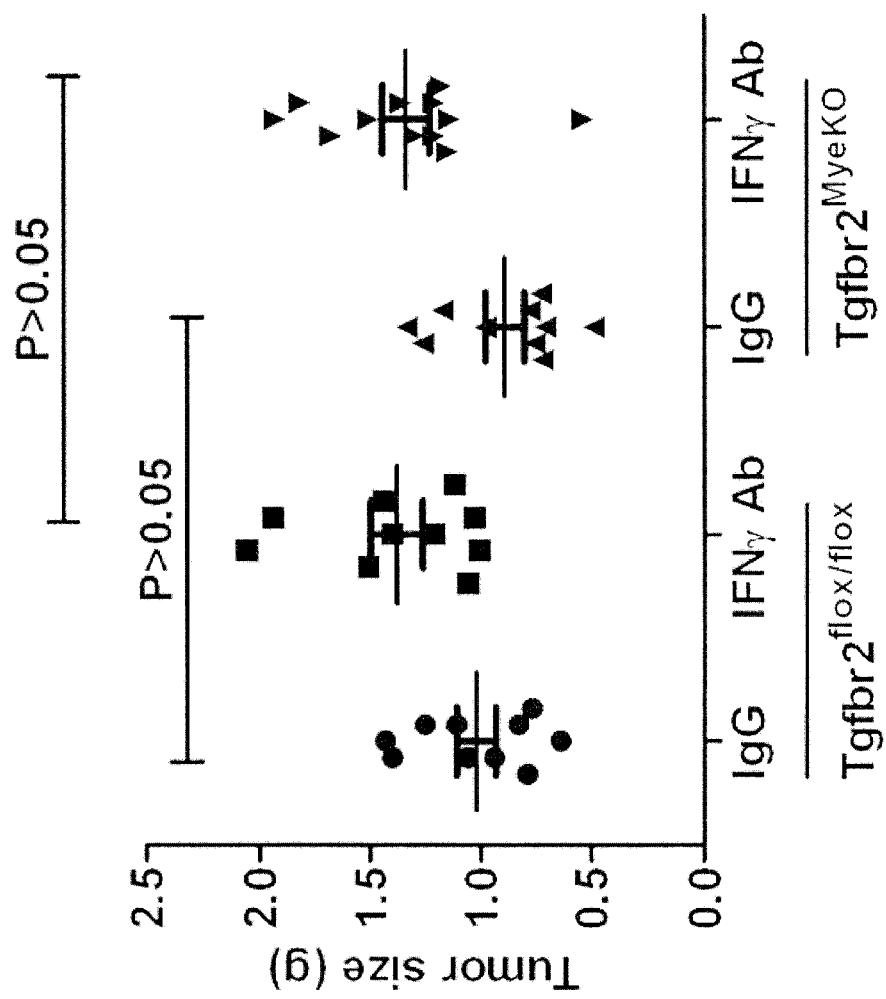

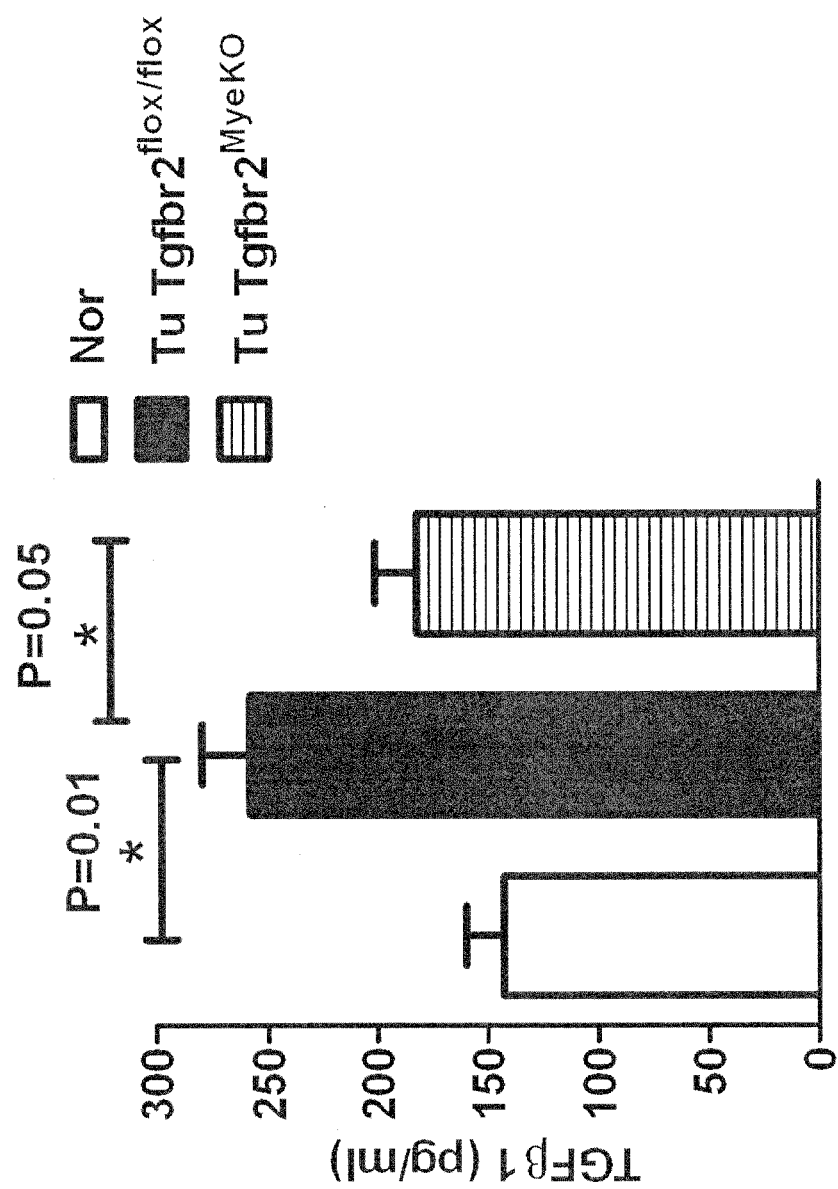

REDUCTION OF TGF BETA SIGNALING IN MYELOID CELLS IN THE TREATMENT OF CANCER

CROSS-REFERENCE TO RELATED APPLICATIONS

This patent application is a divisional of copending U.S. patent application Ser. No. 13/589,769, filed Aug. 20, 2012, which claims the benefit of U.S. Provisional Patent Application No. 61/525,025 filed Aug. 18, 2011, which applications are incorporated by reference.

BACKGROUND OF THE INVENTION

Conventional cancer therapeutic approaches, including radiation and chemotherapy, are nonselective and damage normal cells. Gene therapies have exhibited limited success. This likely is because the vector or virus inefficiently reaches the targeted tumor and/or the agents used in gene therapy interact with normal cells and to yield adverse effects (McCormick, *Nat. Rev. Cancer*, 1: 130-141 (2001), and Scanlon, *Anticancer Res.*, 24: 501-504 (2004)).

TGFβ targeted therapies, such as neutralizing antibodies, small molecular inhibitors, and adenoviruses have been used in preclinical and clinical settings (Dumont et al., *Cancer Cell*, 3: 531-536 (2003)). However, TGFβ is well known to work as a tumor suppressor in early stage tumorigenesis and as a tumor promoter in later stages of tumor progression (Yang et al., *Cancer Res.*, 68: 9107-9111 (2008), and Yang et al, *Trends Immunol.*, 31: 220-227 (2010). The underlying mechanisms for this switch in function are not clear and pose a great challenge for TGFβ targeted therapies. This challenge in TGFβ targeted therapy represents a general problem of cancer biology, as many cancer related molecules demonstrate a dual role of pro- and anti-cancer properties.

Thus, there remains a need for effective and specific treatment of cancer for both animals and humans.

BRIEF SUMMARY OF THE INVENTION

The invention provides a method of inhibiting metastasis in a cancer patient comprising reducing TGFβ receptor II expression in myeloid cells in the cancer patient.

The invention also provides a method of inhibiting metastasis in a cancer patient comprising (a) removing bone marrow comprising myeloid cells from the cancer patient, (b) reducing TGFβ signaling in the myeloid cells of the bone marrow ex vivo to yield TGFβ signaling-deficient bone marrow, and (c) administering the TGFβ signaling-deficient bone marrow to the cancer patient, so as to inhibit metastasis in the cancer patient.

Additionally, the invention provides a method of inhibiting metastasis in a cancer patient comprising transplanting TGFβ receptor II (Tgfbr2)-deficient myeloid cells to the cancer patient.

The invention further provides a vector comprising a Tgfbr2 RNAi nucleic acid sequence operably linked to a myeloid specific promoter.

The invention provides a method of diagnosing cancer in an individual comprising (a) obtaining a sample comprising myeloid cells from the individual; and (b) determining TGFβ receptor II expression in the myeloid cells, wherein increased TGFβ receptor II expression in the myeloid cells relative to a control indicates a diagnosis of cancer in the individual.

The invention also provides a method of modulating TGFβ activity in myeloid cells in a cancer patient comprising administering a regulator of at least one of the GSK3 and PI3K pathways to the patient.

BRIEF DESCRIPTION OF THE SEVERAL VIEWS OF THE DRAWING(S)

FIG. 2 is a graph with the number of 4T1 lung metastases (y-axis) from floxed control Tgfbr2$^{flox/flox}$ (white bar) and Tgfbr2$^{MyeKo}$ (black bar) mice that received injection of 4Ti mammary tumor cells into the #2 mammary fat pad (MFP) (x-axis).

Figure 5:
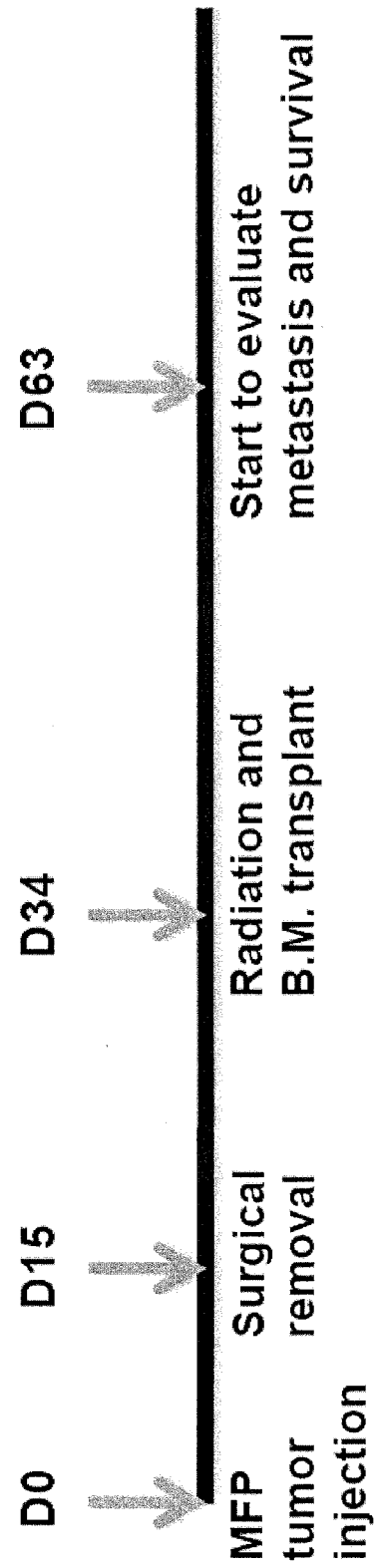

FIG. 5 is a schematic showing the experimental design for adoptive transfer of bone marrow to wild-type tumor-bearing mice. 4T1 cells ($5 \times 10^5$) were injected into mammary fat pad of wild-type mice on day 0 (D0). The tumors were surgically removed on day 15 (D15), and the mice were left to recover until day 34 (D34) after tumor injection (allowing development of tumor invasion and metastasis). On D34, mice received a bone marrow transplant from floxed control Tgfbr2$^{flox/flox}$ or Tgfbr2$^{MyeKO}$ mice. Lung metastasis was examined on day 63 (D63).

FIGS. 6A and 6B are graphs demonstrating the differences in survival and the number of lung metastases between floxed control Tgfbr2$^{flox/flox}$ (●) (n=9) or Tgfbr2$^{MyeKO}$ mice (■) (n=8). FIG. 6A has percent survival on the y-axis and days after tumor injection on the x-axis. FIG. 6B has the number of lung metastases on the y-axis for floxed control Tgfbr2$^{flox/flox}$ (white bar) or Tgfbr2$^{MyeKO}$ (black bar) mice.

FIG. 7 is a graph showing the fold changes in Gr-1+ CD11b+ myeloid cell (MDSC) production (y-axis) in spleen, bone marrow, and peripheral blood for normal (white bar) and 4T1 tumor bearing (D35 tu) (black bar) mice.

Figure 8:
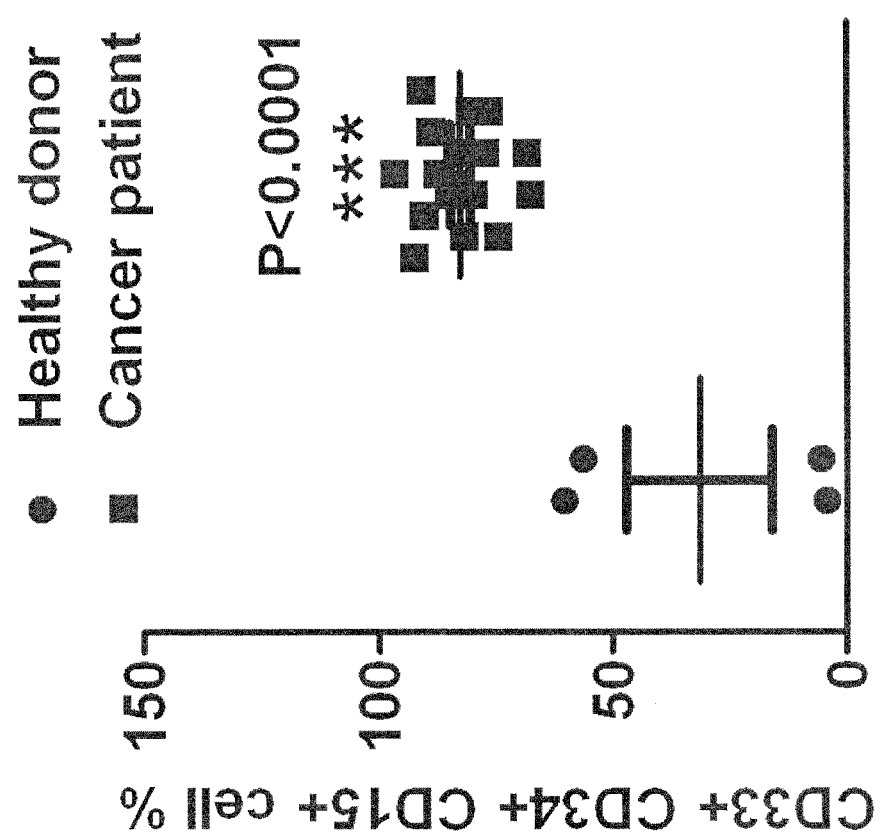

FIG. 8 is a graph showing the percentage of CD33+ CD34+CD15+ cells (y-axis) for healthy donors (●) and lung cancer patients (■). Flow cytometry analysis of immature myeloid cells was performed with anti-CD33, CD34, and CD15 antibodies.

Figure 9A:
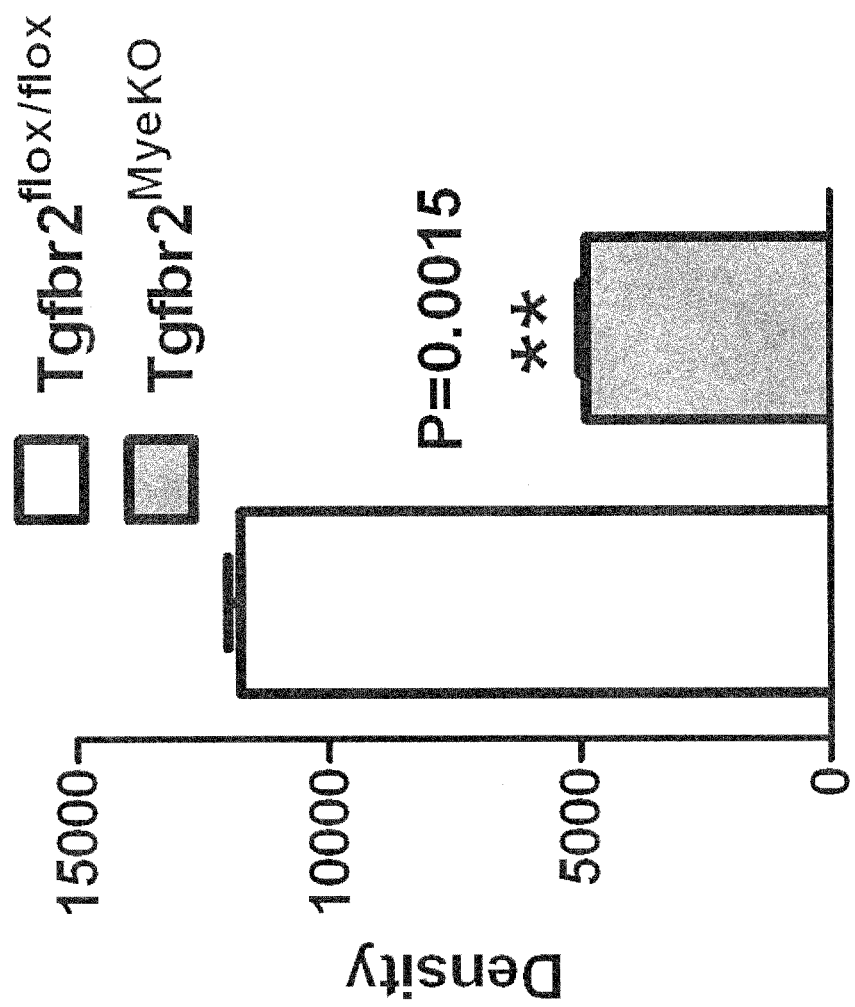
Figure 9B:
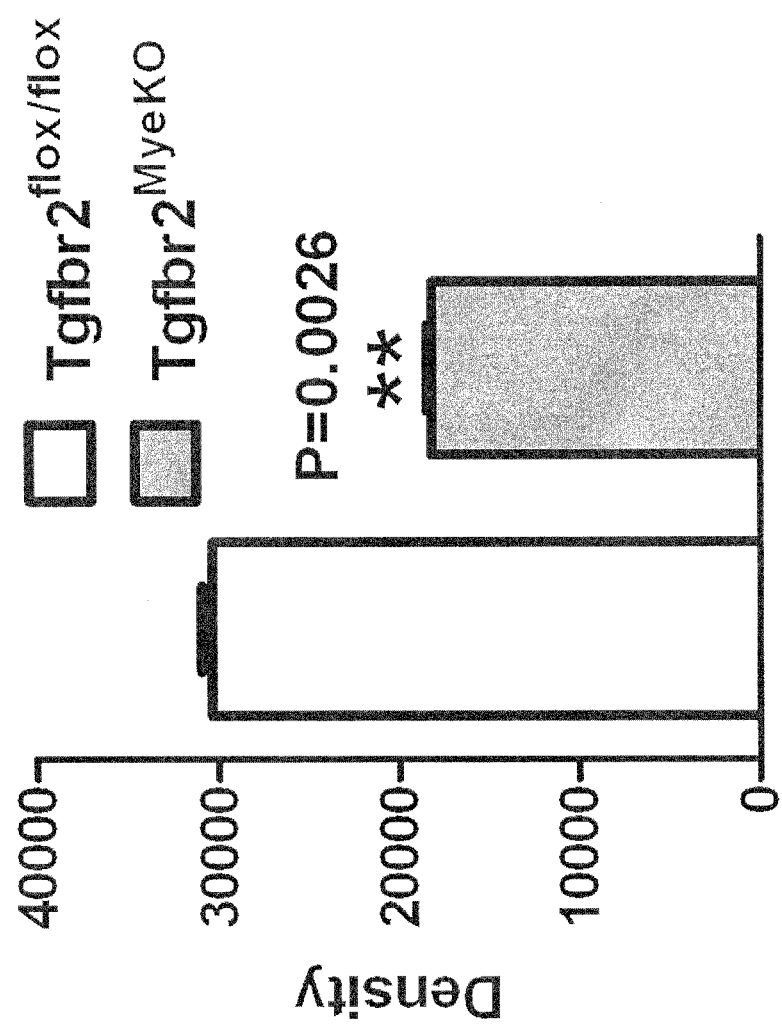

FIGS. 9A and 9B are graphs showing the density of PF4 expression (y-axis) in myeloid cells (9A) and in the premetastatic lungs (9B) of floxed control Tgfbr2$^{flox/flox}$ (white bar) and Tgfbr2$^{MyeKo}$ (black bar) mice.

Figure 9D:
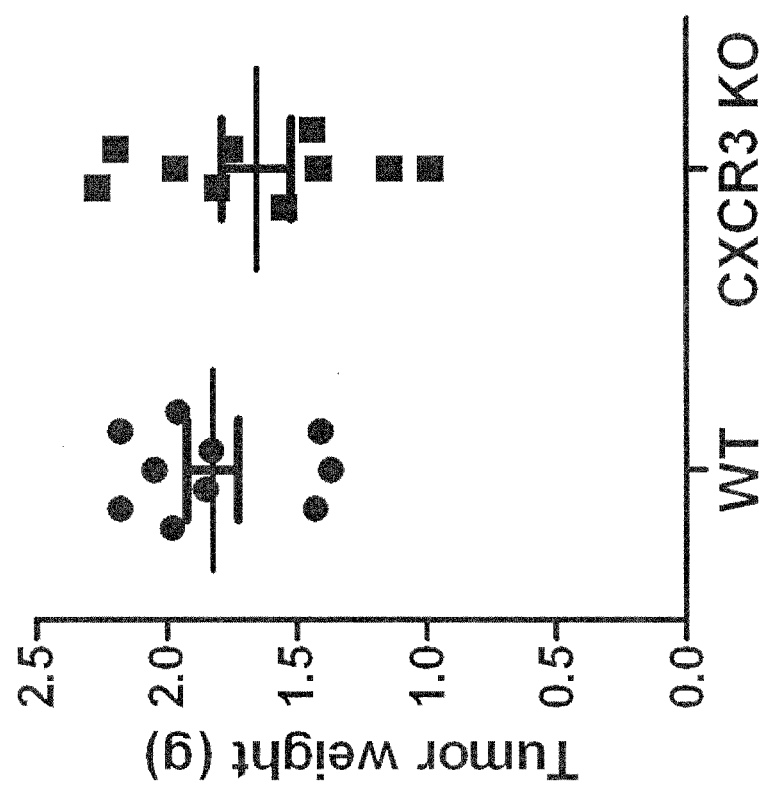

FIGS. 9C and 9D are graphs demonstrating the differences between lung metastases and tumor weight (g) between wild-type (●) and CXCR3 knockout (■) mice that received injection of 4Ti mammary tumor cells into the #2 mammary fat pad. FIG. 9C has the number of lung metastasis on the y-axis. FIG. 9D has tumor weight (g) on the y-axis.

Figure 10A:
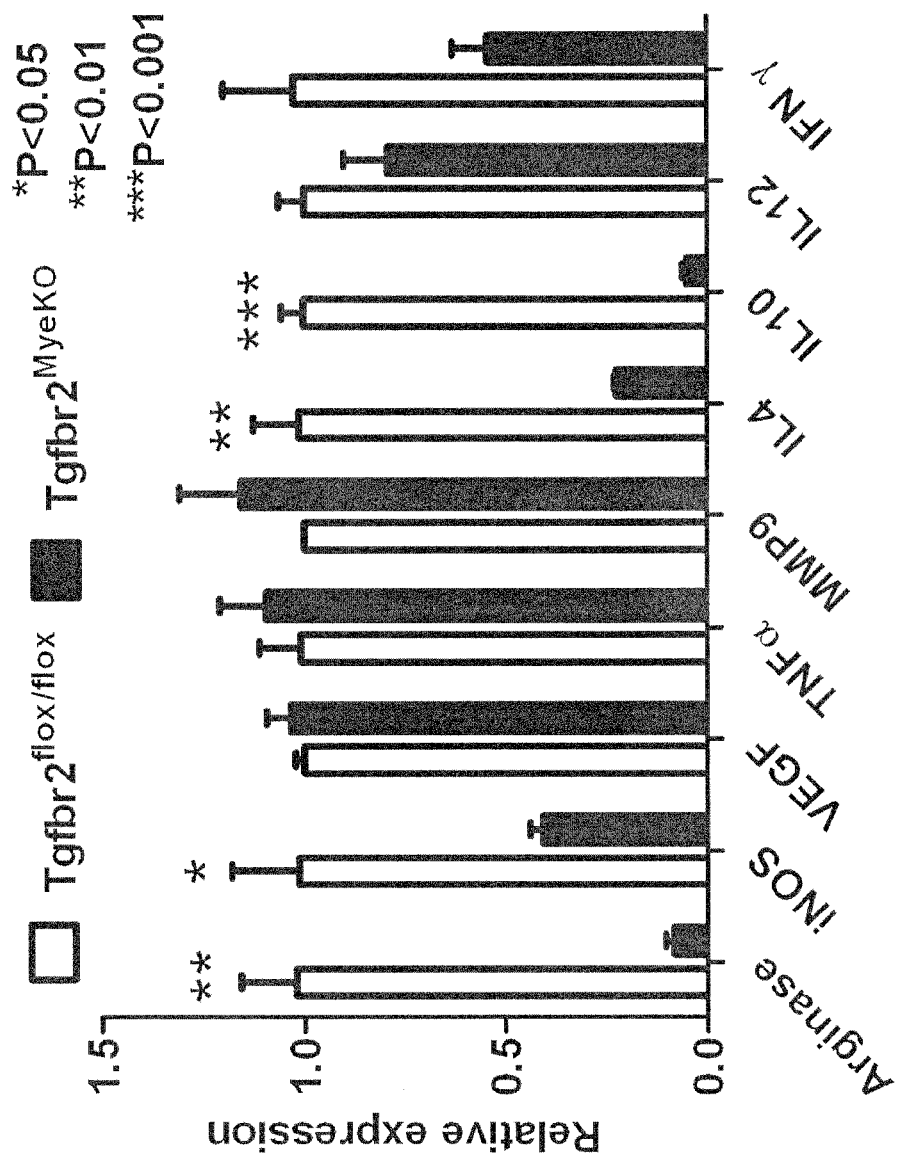
Figure 10B:
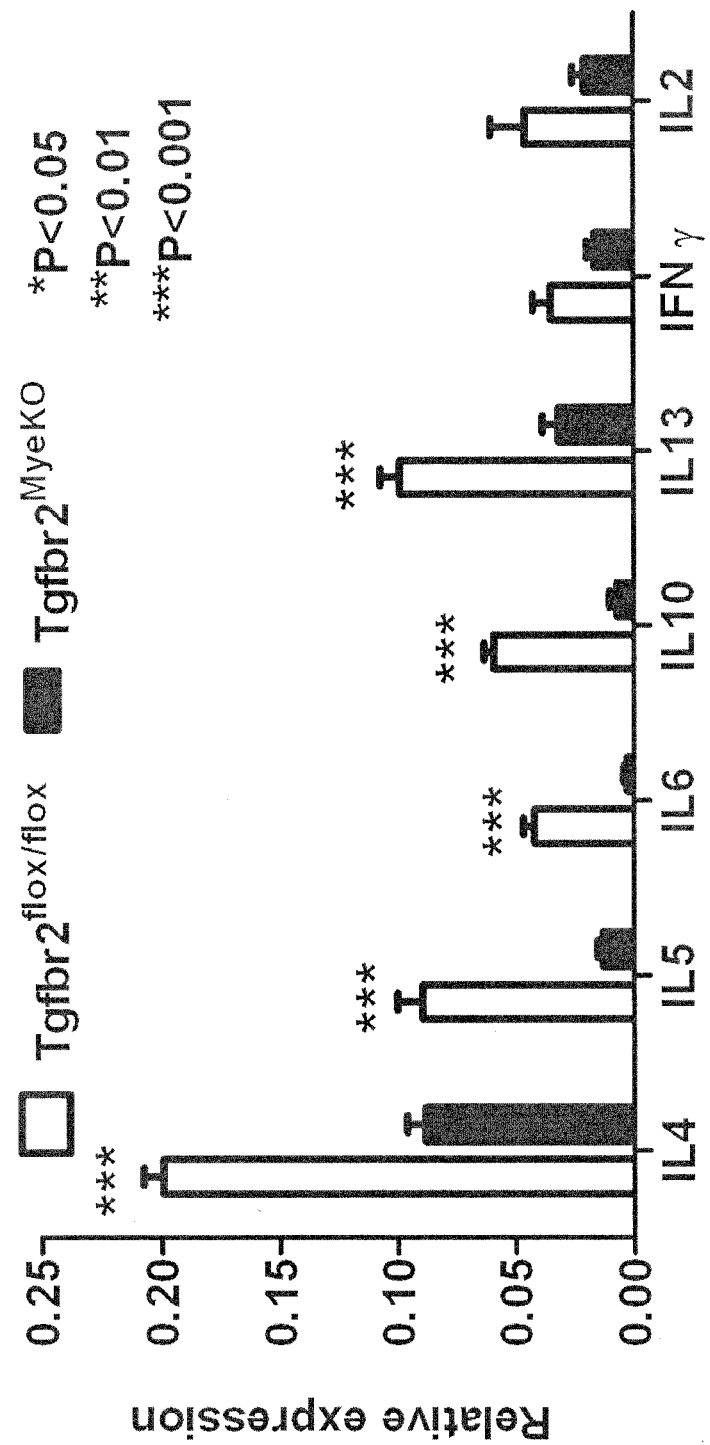

FIGS. 10A and 10B are graphs showing relative expression of cytokines in Gr-1+CD11b+ cells of floxed control Tgfbr2$^{flox/flox}$ (white bar) or Tgfbr2$^{MyeKO}$ (black bar) mice.

FIG. 10A is a graph with relative expression (y-axis) for each of arginase, INOS, VEGF, TNFα, MMP9, IL4, IL-10, IL12, and IFNγ (x-axis). FIG. 10B is a graph with relative expression (y-axis) for each of IL4, IL5, IL6, IL-10, IL13, IFNγ, and IL2 (x-axis) bar.

FIG. 11A is a graph showing the percentage of IFNγ positive CD8+ T cells in the spleen of tumor-bearing Tgfbr2$^{MyeKO}$ (black) mice compared to Tgfbr2$^{flox/flox}$ (white bar) mice.

FIG. 11B is a graph showing the number of IFNγ-producing cells detected by ELISPOT in the spleens of Tgfbr2$^{MyeKO}$ (black bar) and Tgfbr2$^{flox/flox}$ (white bar) mice.

FIGS. 11C and 11D are graphs demonstrating that IFNγ neutralization increased lung metastases (11C) and tumor size (11D) in both Tgfbr2$^{MyeKO}$ and Tgfbr2$^{flox/flox}$ mice. Mice were inoculated with 5×10$^4$ 4T1 cells in the #2 MFP. The mice were treated with IFNγ neutralizing antibody (1 mg on day 1, 3, and 6) or IgG control (0.5 mg on day 9, 12, 15, 18, 21, 24, and 27) through intraperiotoneal injection. For evaluation of lung metastases, mice were euthanized on day 28 after tumor injection.

FIG. 11E is a graph demonstrating TGFβ1 level (pg/mL) in myeloid cells (Gr-1+CD11b+) of wild-type (Nor), tumor-bearing Tgfbr2$^{MyeKO}$, and Tgfbr2$^{flox/flox}$ mice on the y-axis. Sorted Gr-1+CD11b+ cells were cultured overnight and supernatants were collected for TGFβ1 ELISA.

Figure 12A:
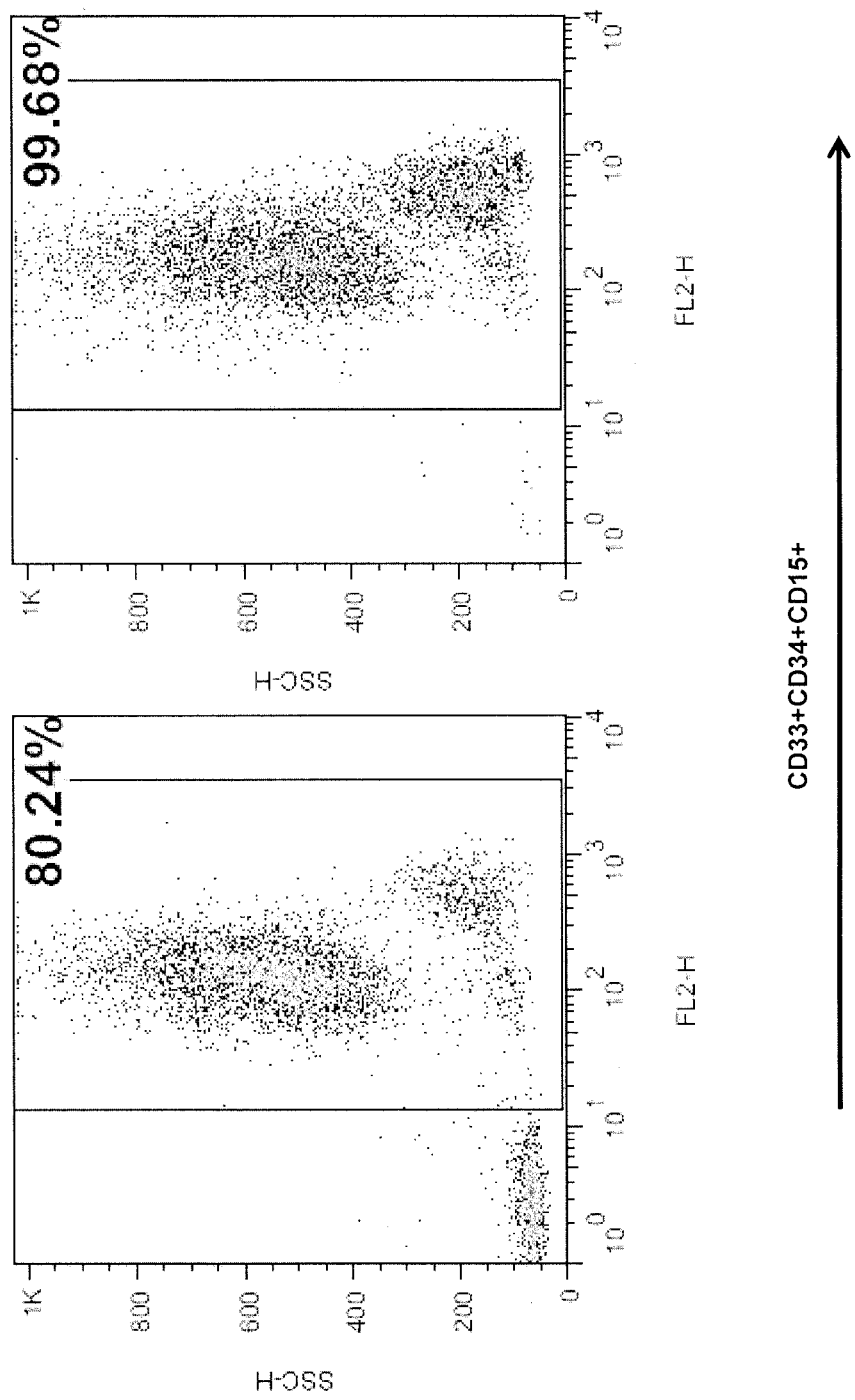

FIG. 12A depicts fluorescence analysis and magnetic cell sorting (MACS) of human immature myeloid cells (CD33+ CD34+CD15+) before (left panel) and after (right panel) sorting.

Figure 12B:
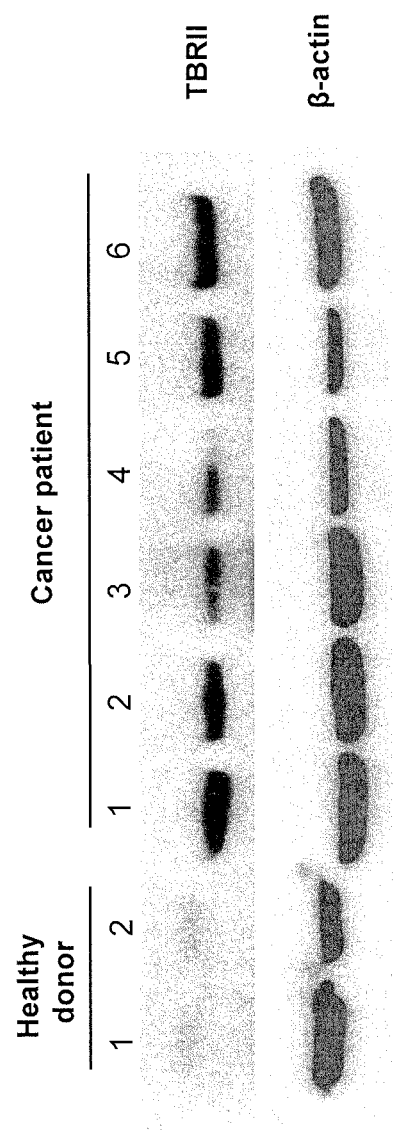

FIG. 12B depicts the results of Western blot analysis of TβRII expression in CD33+CD34+CD15+ myeloid cells, wherein β-actin served as a positive control. Samples from two normal individuals and six later stage lung cancer patients were examined.

DETAILED DESCRIPTION OF THE INVENTION

The inventors discovered that myeloid TGFβ signaling is an essential part of the tumor promoting role of TGFβ. Specifically, the inventors discovered that the expression of TGFβ receptor II in myeloid cells of tumor hosts plays an essential role in metastasis. Increased TGFβ signaling in myeloid cells constitutes a critical part of the tumor-promoting role of TGFβ. When TGFβ receptor II is deleted in myeloid cells, there is a significant decrease in tumor metastasis.

Accordingly, the invention provides a method of inhibiting metastasis in a cancer patient comprising reducing TGFβ signaling in the cancer patient. TGFβ signaling can be reduced by any suitable method known in the art, but is preferably reduced by reducing TGFβ receptor II expression in myeloid cells of the cancer patient.

The cancer patient can be any suitable patient, such as an animal (e.g., mouse, rat, guinea pig, rabbit, hamster, cat, dog, horse, cow, pig, simian, or human) with cancer or who is at risk for cancer.

Non-limiting examples of specific types of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocytic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001).

In one aspect of the invention, metastasis in a cancer patient is inhibited by (a) removing bone marrow comprising myeloid cells from the cancer patient, (b) reducing TGFβ signaling in the myeloid cells of the bone marrow ex vivo to yield TGFβ signaling-deficient bone marrow, and (c) administering the TGFβ signaling-deficient bone marrow to the cancer patient, so as to inhibit metastasis in the cancer patient. The TGFβ signaling deficiency preferably is a result of decreased TGFβ receptor II expression.

TGFβ receptor II is a member of the Ser/Thr protein kinase family and the TGFβ receptor subfamily. The encoded protein is a transmembrane protein that has a protein kinase domain, forms a heterodimeric complex with another receptor protein, and binds TGFβ. This receptor/ligand complex phosphorylates proteins, which then enter the nucleus and regulate the transcription of a subset of genes related to cell proliferation. Alternatively spliced transcript variants encoding different isoforms have been characterized (GenBank Accession Nos. NM_001024847 and NM_003242).

TGFβ receptor II expression can be reduced by any suitable method, such as RNA interference (RNAi), mutation of the nucleic acid sequence encoding TGFβ receptor II (to produce a non-functional TGFβ receptor II), or knockout (deletion of the native gene or portion thereof) of the nucleic acid sequence encoding TGFβ receptor II. Alternatively, TGFβ receptor II activity can be reduced by inhibition of the polypeptide, for example, by administration of TGFβ receptor II-specific antibodies, peptidomimetics, or small molecules.

In another embodiment, TGFβ and/or TGFβ receptor II activity can be mediated (e.g., reduced) by administration of a modifier (e.g., inhibitor or enhancer) of a member of a related signaling pathway (e.g., the GSK3 and PI3K signaling pathways). For example, Example 7 describes the use of a PI3K inhibitor (LY294002), which can be used to target or modify myeloid cells in a cancer patient.

Accordingly, the invention also provides a method of modulating TGFβ and/or TGFβ receptor II activity in myeloid cells in a cancer patient comprising administering a regulator of at least one of the GSK3 and PI3K pathways to the patient. For example, the myeloid cells of the cancer patient can be removed from the cancer patient, contacted with a PI3K inhibitor or GSK3 enhancer, which results in a reduction in TGFβ and/or TGFβ receptor II activity in the myeloid cells, and then reintroduced into the cancer patient. TGFβ and/or TGFβ receptor II activity in the myeloid cells includes, but is not limited to, TGFβ regulation of type 2 cytokines (e.g., IL-10 and IL-4) and PF4 in the myeloid cells.

In one aspect, the invention provides a vector comprising or consisting of a nucleotide sequence that encodes an RNAi agent, which is an RNA molecule that is capable of RNA interference. Such RNA molecules are referred to as siRNA (short interfering RNA that is a short-length double-stranded RNA, including, for example, a short hairpin RNA). The nucleotide sequence that encodes the RNAi agent preferably has sufficient complementarity with a cellular nucleotide sequence of TGFβ receptor II to be capable of inhibiting the expression of TGFβ receptor II.

The siRNA can comprise an antisense code DNA coding for the antisense RNA directed against a region of the TGFβ receptor II gene mRNA and/or a sense code DNA coding for the sense RNA directed against the same region of the TGFβ receptor II gene mRNA. The siRNA can be any suitable length, such as 15-50 (e.g., 20, 25, 30, 35, 40, or 45) nucleotides.

Alternatively, the RNAi agent can be an antisense RNA, which is an RNA strand having a sequence complementary to the TGFβ receptor II gene mRNA. Antisense RNA induces RNAi by binding to the TGFβ receptor II gene mRNA. The antisense RNA can be any suitable length, such as 15-50 (e.g., 20, 25, 30, 35, 40, or 45) nucleotides.

The vector comprising or consisting of a nucleotide sequence that encodes an RNAi agent can be any suitable vector, such as a viral vector, a plasmid, a yeast, a nanoparticle, or naked DNA. Suitable viral vectors, included poxviruses (e.g., orthopox viruses, such as vaccinia viruses, and avian poxviruses, such as fowlpox virus and canarypox virus), adenoviruses, adeno-associated viruses, and retroviruses.

The nucleotide sequence that encodes an RNAi agent can be operably linked to a promoter (in the vector). The promoter preferably is a myeloid-specific promoter so that expression of the RNAi agent is specific to myeloid cells. The CD11b promoter and the c-fes promoter are examples of myeloid-specific promoters.

The RNAi agent, vector, or regulator of at least one of the GSK3 and PI3K pathways can be administered alone or in a composition (e.g., pharmaceutical composition) that can comprise at least one carrier (e.g., a pharmaceutically acceptable carrier), as well as other therapeutic agents. The RNAi agent, vector, or regulator or the respective composition can be administered by any suitable route, including parenteral, topical, oral, or local administration.

The composition (e.g., pharmaceutical composition) can comprise more than one compound or composition of the invention. Alternatively, or in addition, the composition (e.g., pharmaceutical composition) can comprise one or more other pharmaceutically active agents or drugs. Examples of such other pharmaceutically active agents or drugs that may be suitable for use in the composition (e.g., pharmaceutical composition) include anticancer agents. Suitable anticancer agents include, without limitation, alkylating agents; nitrogen mustards; folate antagonists; purine antagonists; pyrimidine antagonists; spindle poisons; topoisomerase inhibitors; apoptosis inducing agents; angiogenesis inhibitors; podophyllotoxins; nitrosoureas; cisplatin; carboplatin; interferon; asparaginase; tamoxifen; leuprolide; flutamide; megestrol; mitomycin; bleomycin; doxorubicin; irinotecan; and taxol, geldanamycin (e.g., 17-AAG), and various anti-cancer peptides and antibodies.

The carrier can be any of those conventionally used and is limited only by physiochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity (other than that desired by the active compounds) under the conditions of use.

The choice of carrier will be determined in part by the particular compound or composition of the invention and other active agents or drugs used, as well as by the particular method used to administer the compound and/or composition. Accordingly, there are a variety of suitable formulations of the composition (e.g., pharmaceutical composition) of the inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the compound of the invention are known, and, although more than one route can be used to administer a particular compound, a particular route can provide a more immediate and more effective response than another route.

Injectable formulations are among those formulations that are preferred in accordance with the invention. The requirements for effective pharmaceutical carriers for injectable compositions are well-known to those of ordinary skill in the art (See, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations are well-known to those of skill in the art. Such formulations are particularly suitable in the context of the invention for application to the skin.

Formulations suitable for oral administration can consist of (a) liquid solutions, such as an effective amount of the compound or composition dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds and compositions of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds and compositions of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The invention also provides a method of diagnosing cancer in an individual comprising (a) obtaining a sample comprising myeloid cells from the individual; and (b) determining TGFβ receptor II expression in the myeloid cells, wherein increased TGFβ receptor II expression in the myeloid cells relative to a control indicates a diagnosis of cancer in the individual.

Expression of TGFβ receptor II mRNA and/or protein can be determined by any suitable method including, but not limited to, PCR (RT-PCR, quantitative RT-PCR), microarrays, Northern blotting, and Western blotting.

The control can be any suitable control, such as an expression level of TGFβ receptor II mRNA and/or protein from myeloid cells of a normal (healthy) individual or group of normal (healthy) individuals.

The individual can be any suitable individual, such as a mammal including a mouse, rat, hamster, guinea pig, rabbit, cat, dog, pig, horse, cow, or primate (e.g., human).

The following examples further illustrate the invention but, of course, should not be construed as in any way limiting its scope.

EXAMPLE 1

This example demonstrates the generation of a myeloid-specific TGFβ receptor II knockout mouse.

Myeloid cells play an important role in tumor progression. They suppress host immune surveillance and influence the tumor microenvironment (see, e.g., Gabrilovich et al., *Nat. Rev. Immunol.*, 9: 162-174 (2009); Pollard, *Nat. Rev. Immunol.*, 9: 259-270 (2009); Mantovani, *Nature*, 457: 36-37 (2009), Fridlender et al., *Cancer Cell*, 16: 183-194 (2009); Balkwill et al., *Nature*, 431: 405-406 (2004), Yang et al., *Cancer Cell*, 6: 409-421 (2004); and Yang et al., *Cancer Cell*, 13: 23-35 (2008)). Myeloid cells are also present in the lungs prior to tumor cell arrival and contribute to pre-metastatic niche formation and environment alteration (see Kaplan et al., *Nature*, 438: 820-827 (2005); and Yan et al., *Cancer Res.*, 70: 6139-6149 (2010)). These include tumor-associated macrophages (TAM, Mac-1+ or F4/80+ cells), Gr-1+CD11 b+ cells or myeloid derived suppressor cells (MDSCs), and tumor associated neutrophils (TAN, CD11b+Ly6G+ cells). One of the most important properties of these cells is the increased TGFβ production and increased Th2 polarization (see, e.g., Yang, et al., *Cancer Cell*, 13: 23-35 (2008); and Flavell et al., *Nat. Rev. Immunol.* 10: 554-567 (2010)). However, there are no reports as to how TGFβ signaling in myeloid cells affects tumor phenotype.

Figure 1A:
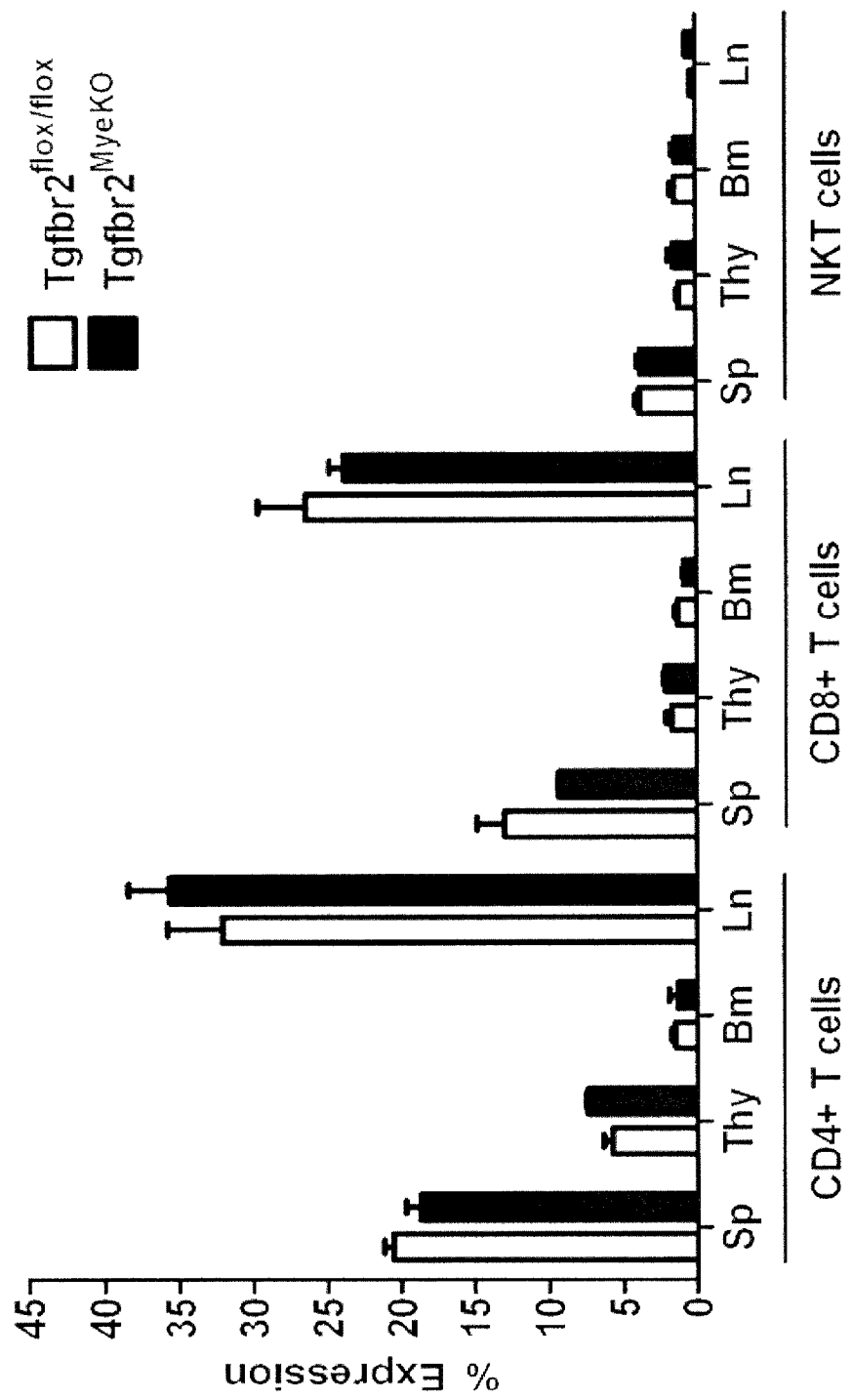
FIGS. 1A and 1B are graphs with percent expression (y-axis) of immune cells from spleen (sp), thymus (thy), bone marrow (bm), and lymph node (ln) (x-axis) for floxed control Tgfbr2$^{flox/flox}$ (white bar) and Tgfbr2$^{MyeKo}$ (black bar) mice. Expression of CD4+ T cells, CD8+ T cells, NKT cells, NK cells, B cells, MDSCs (Gr-1+CD11b+), and macrophages are represented.
Figure 1B:
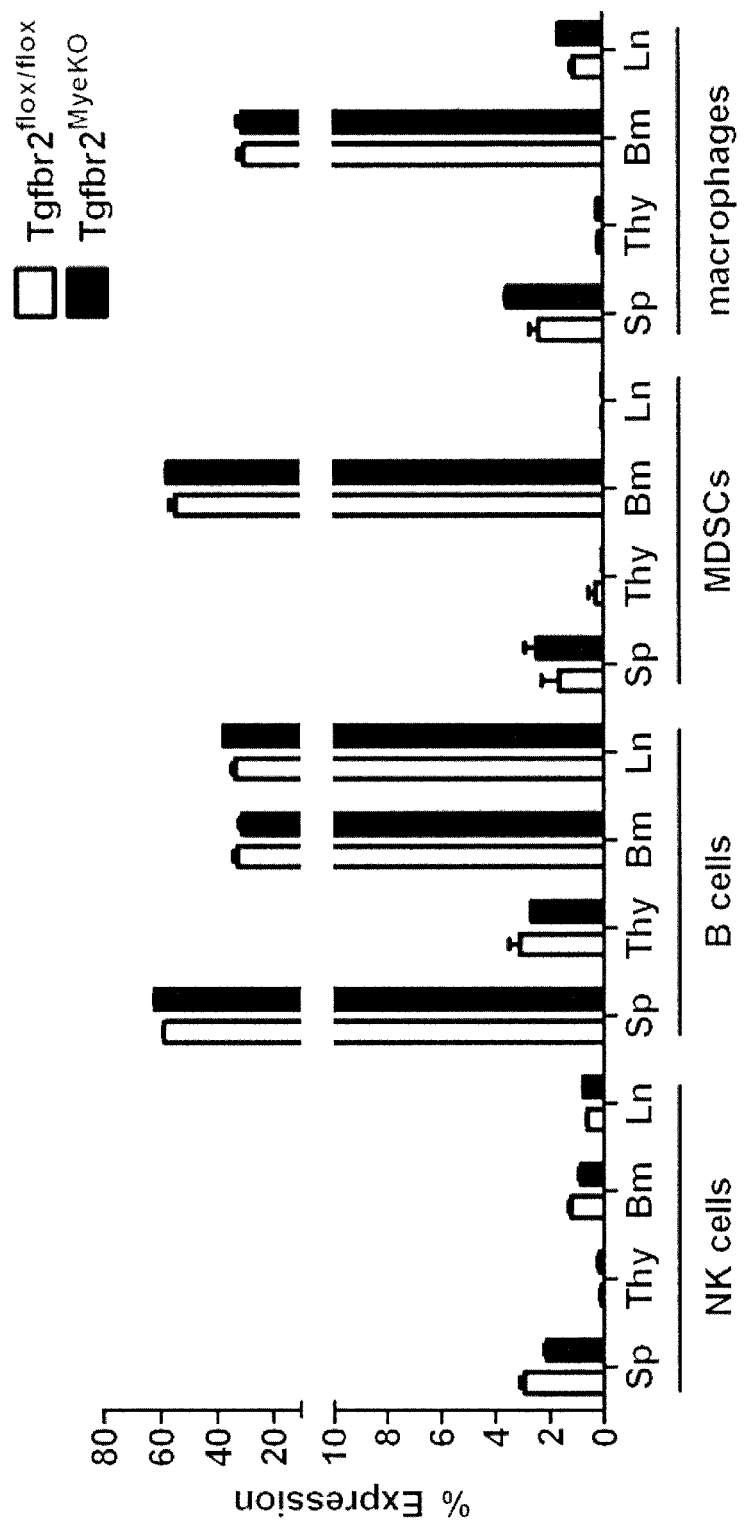

To investigate the effect of myeloid specific abrogation of TGFβ signaling on tumor phenotype, knock out mice with a specific deletion of the TGFβ receptor II in myeloid cells)(Tgfbr2$^{MyeKO}$) were generated. Mice with targeted deletion of Tgfbr2 in myeloid cells) (Tgfbr2$^{MyeKO}$) were generated through the cross breeding of floxed Tgfbr2 (Tgfbr2$^{flox/flox}$) (see, e.g., Chytil et al., *Genesis*, 32: 73-75 (2002); and Forrester et al., *Cancer Res.*, 65: 2296-2302 (2005)) mice with LysM-Cre transgenic mice (in C57BL/6 and 129 background). Mice heterozygous for LysM-Cre and heterozygous for the floxed Tgfbr2 allele were further bred with wild-type Balb/c or C57BL/6 for 10 generations to generate a Balb/c or C57BL/6 background. LysM-Cre transgenic mice have been well characterized and used in many other studies to delete floxed genes specifically in myeloid cells, both neutrophils and monocytes/macrophages (see, e.g., Sinha et al., *J. Immunol.*, 173: 1763-1771 (2004); Sun et al., *Blood*, 104: 3758-3765 (2004); and Hazenbos et al., *Blood*, 104: 2825-2831 (2004)). The Tgfbr2$^{MyeKO}$ mice appeared to be normal with no alteration in hematopoiesis (see FIGS. 1A and 1B). This includes macrophages (CD11b+F4/80+), MDCSs (Gr-1+CD11b+), B cells (B220), CD4+ T cells, CD8+ T cells, as well as NK cells (NK 1.1), and NKT cells (NK1.1 and TCRβ) derived from spleen, thymus, bone marrow and lymph nodes (FIGS. 1A and 1B).

EXAMPLE 2

This example demonstrates that reduced expression of TGFβ signaling reduces lung metastasis.

The 4T1 mammary tumor model shares many characteristics with human breast cancer, particularly its ability to spontaneously metastasize to the lungs. In an orthotopic metastasis design, 5×10$^4$ 4T1 cells in 50 μL PBS were injected into the #2 mammary fat pad (MFP) of Tgfbr2$^{MyeKO}$ and floxed control Tgfbr2$^{flox/flox}$ mice. Mice were sacrificed 28 days later, and the number and size of lung metastasis was evaluated. Tgfbr2$^{MyeKO}$ mice showed a decreased ability to support tumor metastasis after injection of 4T1 mammary tumor cells (see FIG. 2), with no difference in primary tumor size.

Figure 3:
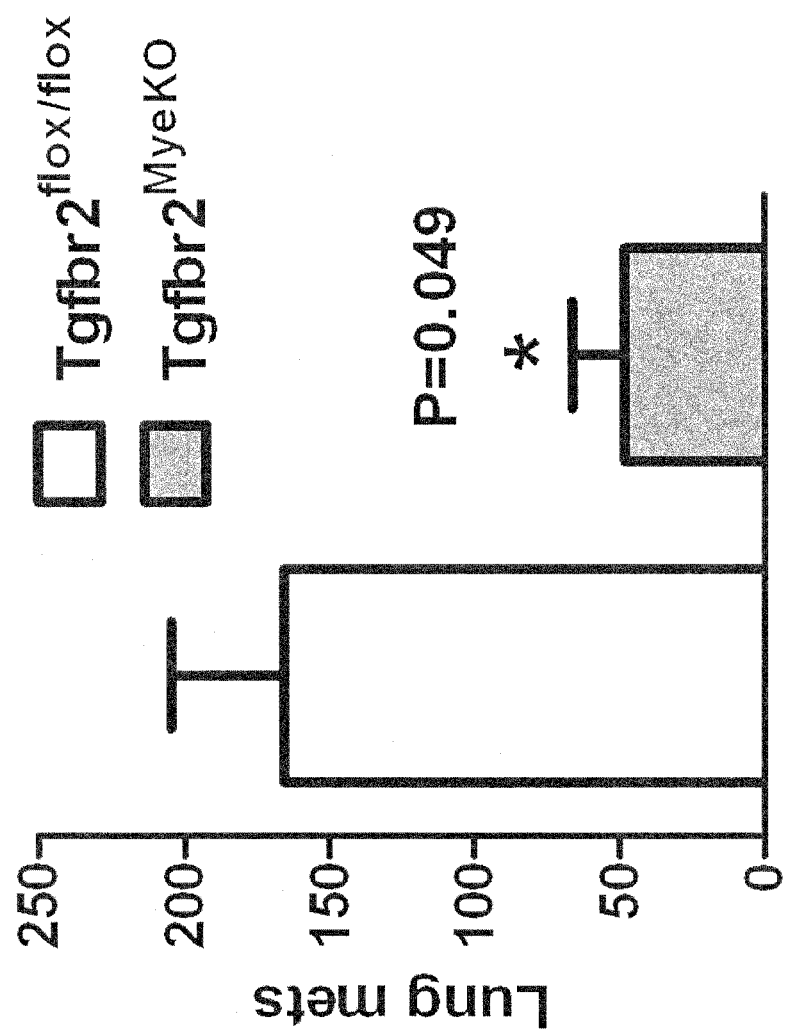
FIG. 3 is a graph with the number of 4T1 lung metastases (y-axis) for floxed control Tgfbr2$^{flox/flox}$ (white bar) and Tgfbr2$^{MyeKo}$ (black bar) mice that received a tail vein injection of $5 \times 10^5$ 4T1 tumor cells (x-axis)
Figure 4:
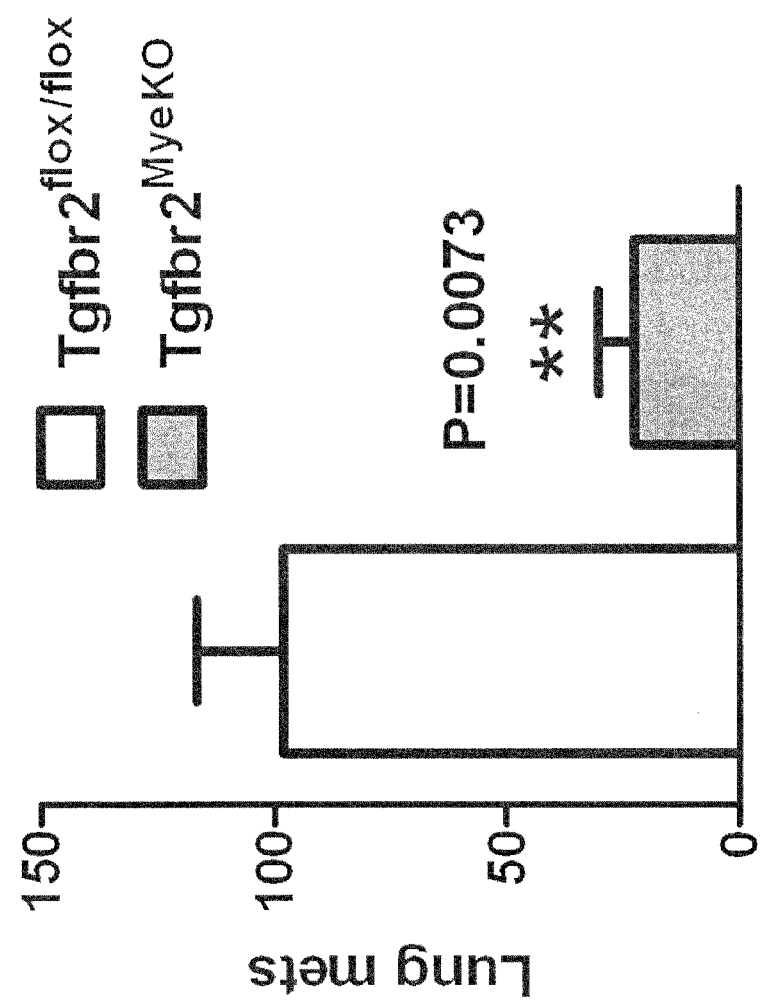
FIG. 4 is a graph with the number of 3LL Lewis lung metastases on the y-axis for floxed control Tgfbr2$^{flox/flox}$ (white bar) and Tgfbr2$^{MyeKo}$ (black bar) mice that received tail vein injection of 3LL Lewis lung cancer cells (x-axis).

In an experimental metastasis design, 2×10$^5$ 4T1 cells were injected into the tail vein of Tgfbr2$^{MyeKO}$ and floxed control Tgfbr2$^{flox/flox}$ mice. The size of tumors was determined by direct measurement of tumor dimensions at 2-3 day intervals using calipers. The number of lung metastasis was evaluated when the mice were euthanized at day 25 after injection. There was a significant reduction in metastasis in Tgfbr2$^{MyeKO}$ mice (see FIG. 3). This result was recapitulated in the LLC experimental metastasis model in which Tgfbr2$^{MyeKO}$ mice in a C57BL/6 background were injected in the tail vein with or 2.5×10$^5$ LLC cells and sacrificed at day 21 after injection (see FIG. 4).

These data support that decreased expression of TGFβ signaling results in a decrease of lung metastasis in a mouse model.

EXAMPLE 3

This example demonstrates that the inventive methods inhibit metastasis.

To further confirm the inhibitory effect of myeloid-specific Tgfbr2 deletion on tumor metastasis, Tgfbr2$^{MyeKO}$ bone marrow (B.M.) was transplanted into wild-type mice bearing 4T1 tumors. 5×10$^5$ 4T1 cells were injected into the #4 MFP on day 0. To better model clinical metastatic disease the primary tumor was surgically removed on day 15 and metastasis allowed to continue until day 34 allowing the mice to develop tumor invasion and metastasis. On day 34, the mice were irradiated and subjected to B.M. transplantation from either Tgfbr2Mye$^{KO}$ mice or Tgfbr2$^{flox/flox}$ control mice. Lung metastases were examined on day 63 and thereafter (see FIG. 5).

100% survival of the mice that received B.M. from the Tgfbr2$^{MyeKO}$ mice was observed, whereas approximately 55% of the mice that received B.M. from Tgfbr2$^{flox/flox}$ control mice exhibited decreased survival (see FIG. 6A). In addition, a significantly reduced number of lung metastases were observed in mice that received Tgfbr2$^{MyeKO}$ B.M. relative to those that received control B.M. (see FIG. 6B).

These data suggest that myeloid-specific TGFβ signaling constitutes an essential part of the metastasis-promoting role of TGFβ. When Tgfbr2 is ablated in myeloid cells, tumor metastasis is significantly decreased. Notably, this experimental model uncovers mechanisms different from those observed in mice with Tgfbr2 deletion in FSP+ fibroblasts, which develop invasive squamous cell carcinoma in the fore-stomach, and intraepithelial neoplasia in the prostate (see, e.g., Bhowmick et al., *Science*, 303: 848-851 (2004)). The consequences of myeloid-specific Tgfbr2 ablation are also different from deletion of Smad4 signaling in T cells, which induces gastrointestinal cancer development (see, e.g., Kim et al., *Nature*, 441: 1015-1019 (2006)).

Instead, these data are reminiscent of those observed following blockade of TGFβ signaling in T cells using CD4dnTGF-RII mice, which confers resistance to an EL-4 lymphoma or a B16-F10 melanoma tumor challenge (see, e.g., Gorelik et al., *Nat. Med.*, 7: 1118-1122 (2001)). However, those mice developed an autoimmune pathology that is not seen in the current mouse model. The lack of pathology in the current mouse model is likely due to the fact that myeloid cells are massively expanded under tumor conditions (see FIG. 7). In particular, Gr-1+CD11b+ cells, which produce large quantities of TGFβ, constitute the majority of the tumor-associated myeloid cells in the 4T1 mammary tumor and Lewis lung carcinoma (LLC) models. Splenic Gr–1+CD11b+ cells from tumor-bearing mice expressed significantly higher levels of TGFβ receptor II compared with their non-tumor-bearing counterparts.

These data support that the specific deletion of myeloid Tgfbr2 produces a pronounced antitumor effect with very few adverse effects.

EXAMPLE 4

This example demonstrates the correlation between TGFβ receptor II overexpression and cancer.

Immature myeloid cells are overproduced in tumor hosts including patients with a variety of cancers (see, e.g., Yang et al., *Cancer Cell*, 6: 409-421 (2004); and Almand et al., *J. Immunol.*, 166: 678-689 (2001)). In humans, these cells have been identified as myeloid linage marker CD33+CD34+ CD15+ cells (Yang et al., *Cancer Cell*, 6: 409-421 (2004); Zea et al., *Cancer Res.*, 65: 3044-3048 (2005); Srivastava et al., *Cancer Immunol. Immunother.*, 57: 1493-1504 (2008); Hoechst et al., *Hepatology*, 50: 799-807 (2009); and Chalmin et al., *J. Clin. Invest.*, 120: 457-471 (2010)).

To investigate whether TGFβ receptor II was over-expressed in these human myeloid cells, peripheral blood from 16 patients with metastatic non-small cell lung cancers was collected. CD33+CD34+CD15+ myeloid cells accounted for approximately 85% of the total leukocytes in these patients, clearly higher than that of healthy individuals (28%, n=4) (see FIG. 8). Sorted immature myeloid cells from cancer patients also showed overtly increased TGFβ receptor II expression compared to those from healthy individuals (see FIGS. 12A-B), suggesting a strong clinical relevance for TGFβ receptor II over-expression in myeloid cells.

Furthermore, the expression of Tgfβ1 and TGFβ receptor II mRNA in human peripheral blood mononuclear cells in cohorts of lung cancer (GSE20189) and breast cancer (GSE27567) was determined. The lung cancer and breast cancer datasets were analyzed by Genespring GX 10.0 software. TGFβ receptor II expression correlated with the degree of malignancy in the lung and breast cancer datasets. These results indicate that TGFβ receptor II expression in monocytes can be used for diagnosis and/or prognosis of cancer.

The over-expression of TGFβ receptor II in both human and mouse myeloid cells from cancer hosts strongly supports that TGFβ receptor II signaling in myeloid cells affects tumor progression and metastasis.

EXAMPLE 5

This example demonstrates the characterization of reduced TGFβ signaling.

Gr-1+CD11b+ cells are present in the premetastatic lung (prior to tumor cell arrival). They change the lung into an inflammatory and proliferative environment, diminish immune protection, and promote metastasis through aberrant vasculature formation. The premetastatic lung is characterized by increased growth factors, inflammatory cytokines, and chemokines, such as the chemokine PF4. PF4, also known as CXCL4, was significantly increased in lungs of 4T1 tumor bearing mice at day 10 and 14 when compared with non-tumor control mice.

PF4 belongs to a CXCL chemokine family that includes CXCL9, CXCL10, and CXCL11. These chemokines signal through CXCR3, a G protein coupled receptor. Interestingly, other than PF4, there was no change in the expression of other members of this chemokine family (i.e., CXCL9, CXCL10, and CXCL11). Notably, the deletion of Tgfbr2 decreased PF4 expression in myeloid cells (see FIG. 9A) and in the premetastatic lungs of Tgfbr2$^{MyeKO}$ mice (see FIG. 9B).

To determine the functional significance of decreased PF4/CXR3 signaling in tumor metastasis, CXCR3 knockout mice (see, e.g., Pan et al., *J. Immunol.*, 176: 1456-1464 (2006)) were used. Deletion of CXCR3 dramatically decreased the number of lung metastasis in the mice that received 4T1 tumor injection in the #2 MFP (see FIG. 9C) with no effect on primary tumor size or weight (see FIG. 9D).

These data support that PF4/CXCR3 chemokine axis plays a specific and critical role in 4T1 tumor lung metastasis.

EXAMPLE 6

This example demonstrates the further characterization of reduced TGFβ signaling.

TGFβ signaling is a critical mediator of polarization of myeloid cells. Therefore, Th1/Th2 cytokine expression of Gr-1+CD11b+ cells was examined. Interestingly, the expression of Th2 type cytokines, including IL-10 and IL4, was reduced in myeloid cells with the Tgfbr2 deletion compared to controls, with no difference in Th1 type cytokine production (e.g., IL-12 and IFNγ) (see FIG. 10A). There also was a reduction in arginase and iNOS levels (see FIG. 10A), which are implicated in the immune suppression effects of Gr-1+CD11b+ cells. These results were further confirmed with a cytokine protein array assay (see FIG. 10B).

Since tumor associated myeloid cells exert immune suppression through inhibiting multiple immune cell function in tumor hosts, whether myeloid-specific Tgfbr2 deletion resulted in an improved function of CD4, CD8, B, NK, or macrophage cells was examined. Single cell suspensions from spleen were made, and IFNγ ELISPOT and intracellular cytokine staining of IL2, IL-10, IL4 (CD4 T cells), IFNγ, IL2 (CD8 T cells), CD69, 41BB (B cell function), IFNγ (NK cell function), as well as IL12 and IL-10 (macrophage function) were performed between Tgfbr2$^{MyeKO}$ and the control littermates.

An increased percentage of IFN-γ positive CD8+ T cells was observed in the spleen of tumor-bearing Tgfbr2$^{MyeKO}$ mice compared to Tgfbr2$^{flox/flox}$ mice (see FIG. 11A). No difference was found in other cytokines or cell types. This was consistent with the increased number of IFN-γ producing cells detected by ELISPOT in the spleens of Tgfbr2$^{MyeKO}$ mice (see FIG. 11B). Importantly, systemic neutralization of IFN-γ diminished the inhibitory effect of myeloid Tgfbr2 deletion on metastasis (see FIG. 11C) with no effect on tumor size (see FIG. 11D).

This data suggests that genetic inactivation of TGFβ receptor II in myeloid cells likely decreases immune suppression in tumor bearing hosts through improved Th1/Th2 balance and elevated IFNγ production in CD8 T cells, which likely contributes to reduced tumor metastasis in Tgfbr2$^{MyeKO}$ mice.

Gr-1+CD11b+ cells are one of the major sources of TGFβ in the tumor bearing host. Deletion of Tgfbr2 decreased TGFβ1 production in Gr-1+CD11b+ cells (see FIG. 11E), suggesting possible autocrine and/or paracrine loops that enhance TGFβ production and signaling in myeloid cells. It is not clear whether TGFβ production directly converts myeloid cells from an M1 to M2 phenotype or is the result of M2 TAM polarization. The data show that deletion of myeloid Tgfbr2 induced a decrease of both Th2 cytokines and TGFβ 1 production, which was associated with increased IFN-γ expression in CD8 T cells. This likely improves the host immune surveillance in the Tgfbr2$^{MyeKO}$ mice. Taken together, these studies demonstrate that myeloid-specific TGFβ signaling is a significant part of the tumor-promoting effects of TGFβ, and provides a therapeutic opportunity for new approaches to cancer therapy.

EXAMPLE 7

This example demonstrates the mechanism of reduced TGFβ signaling.

To determine the mechanisms underlying decreased Th2 cytokine or PF4 expression in myeloid cells of Tgfbr2$^{MyeKO}$ mice, the expression of potentially relevant genes was determined. Increased expression of glycogen synthase kinase 3 (GSK3) and NFκB was observed in Gr-1+CD11b+ cells sorted from Tgfbr2$^{MyeKO}$ mice. GSK3 is a serine/threonine protein kinase that mediates the addition of phosphate molecules into serine and threonine amino acid residues. GKS3 has been implicated in the production of inflammation-associated cytokines (see, e.g., Park et al., *Nat. Immunol.*, 12: 607-615 (2011); and Woodgett et al., *Nat. Immunol.*, 6: 751-752 (2005)).

Gr-1+CD11b+ myeloid cells were sorted with MACS from Tgfbr2$^{MyeKO}$ and cultured for 6 hours with an inhibitor of GSK3 (SB216763, Sigma) or PI3K (LY294002, Calbiochem) at different doses (2, 5, and 10 μM for the GSK3 inhibitor; 5, 10, and 20 μM for the PI3K inhibitor). SB216763 is a potent and selective ATP-competitive inhibitor of the serine/threonine protein kinas GSK α and β.

LY294002 competitively inhibits ATP binding of the catalytic subunit of PI3 kinases, consequently enhancing GSK3 activity. GSK3 Western blotting was performed to detect inhibiting activity. The expression of IL-10, IL-4, and PF4 was examined using Western blotting and quantitative PCR.

The GSK3-specific inhibitor (SB216763) reversed the down-regulation of IL-10, IL-4, and PF4 in the myeloid cells lacking Tgfbr2 at both the mRNA level and protein level. The inhibitor of PI3K (LY294002), the upstream mediator of GSK3, resulted in the inverse effect of GSK3 inhibition (i.e., decreased IL-10, IL4, and P4). This is consistent with a negative regulatory role of PI3K on GSK3 that promotes inhibitory phosphorylation of GSK3. Inhibition of NFκB with a specific inhibitor (BMS-345541) did not show a significant effect. These data indicate that TGFβ regulation of Th2 and PF4 likely is mediated by the PI3K and GSK3 signaling pathways. Therefore, PI3K inhibitors (e.g., LY294002) and GSK3 enhancers can be used to target or modify myeloid cells in cancer patients to inhibit cancer and/or metastasis.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inhibiting metastasis in a cancer patient comprising reducing TGFβ receptor II expression in myeloid cells in the cancer patient, wherein the TGFβ receptor II expression is reduced by:
   (a) mutating the nucleic acid sequence encoding TGFβ receptor II in myeloid cells, or
   (b) deleting the nucleic acid sequence encoding TGFβ receptor II or a portion thereof in myeloid cells.

2. The method of claim 1, wherein the myeloid cells are removed from the cancer patient prior to the reduction in TGFβ receptor II expression and the myeloid cells are administered to the cancer patient following the reduction in TGFβ receptor II expression.

3. The method of claim 1, wherein the cancer patient is an animal.

4. The method of claim 3, wherein the cancer patient is a human.

5. The method of claim 1, wherein the metastasis is lung metastasis.

6. The method of claim 1, wherein the patient has breast cancer or lung cancer.

* * * * *